United States Patent
Li et al.

(10) Patent No.: US 8,784,484 B2
(45) Date of Patent: Jul. 22, 2014

(54) ADJUSTABLE ANNULOPLASTY RING SUPPORT

(75) Inventors: XueMei Li, Shoreview, MN (US); Melinda K. Kovach, Plymouth, MN (US); Susan E. Clegg, White Bear Lake, MN (US); Scott Martin, Hugo, MN (US); Rebecca Volovsek, Hudson, WI (US)

(73) Assignee: St. Jude Medical, Inc., St. Paul, MN (US)

( * ) Notice: Subject to any disclaimer, the term of this patent is extended or adjusted under 35 U.S.C. 154(b) by 153 days.

(21) Appl. No.: 13/147,240

(22) PCT Filed: Feb. 1, 2010

(86) PCT No.: PCT/US2010/000276
§ 371 (c)(1),
(2), (4) Date: Nov. 16, 2011

(87) PCT Pub. No.: WO2010/090721
PCT Pub. Date: Aug. 12, 2010

(65) Prior Publication Data
US 2012/0078359 A1    Mar. 29, 2012

Related U.S. Application Data

(60) Provisional application No. 61/206,968, filed on Feb. 6, 2009.

(51) Int. Cl.
*A61F 2/24*    (2006.01)

(52) U.S. Cl.
USPC ........................................................ 623/2.37

(58) Field of Classification Search
USPC ...................... 623/2.17, 2.37–2.39
See application file for complete search history.

(56) References Cited

U.S. PATENT DOCUMENTS

| 5,766,240 A | * | 6/1998 | Johnson | 623/2.39 |
| 2005/0027352 A1 | * | 2/2005 | Cosgrove et al. | 623/2.11 |

FOREIGN PATENT DOCUMENTS

WO    99/49816 A1    10/1999

OTHER PUBLICATIONS

International Search Report, PCT/US2010/000276, dated May 11, 2010.

* cited by examiner

*Primary Examiner* — Thomas J Sweet
*Assistant Examiner* — Christopher D Prone
(74) *Attorney, Agent, or Firm* — Lerner, David, Littenberg, Krumholz & Mentlik, LLP

(57) ABSTRACT

A support for an adjustable annuloplasty ring generally includes a body and a groove. The body has a first end, a second end and an outer surface. The body may also include an inner surface defining a longitudinal bore. The outer surface is configured to slidably receive an annuloplasty ring and a length of adjustable suture. The groove is formed along at least a portion of the outer surface of the body and is dimensioned to receive at least a portion of the suture.

16 Claims, 2 Drawing Sheets

ADJUSTABLE ANNULOPLASTY RING SUPPORT

CROSS-REFERENCE TO RELATED APPLICATIONS

This application is a national phase entry under 35 U.S.C. §371 of International Application No. PCT/US2010/000276, filed Feb. 1, 2010, published in English, which claims the benefit of the filing date of U.S. Provisional Patent Application No. 61/206,968, filed Feb. 6, 2009, the disclosure of which is hereby incorporated herein by reference.

BACKGROUND OF THE INVENTION

The present disclosure relates to mitral and tricuspid valve repair and, more particularly, to apparatus and methods for supporting an adjustable annuloplasty ring.

During a mitral or a tricuspid valve repair, an adjustable annuloplasty ring may be used to return the valve annulus to its natural anatomical shape. The adjustable annuloplasty ring may include an adjustment suture used to adjust the circumference of the annuloplasty ring.

During manufacture, both the annuloplasty ring and its adjustment suture may be subjected to sterilization and heat setting processes. The annuloplasty ring and/or adjustment suture may be placed on a mandrel during these processes. The annuloplasty ring and adjustment suture are then transferred to a support or holder. The support or holder secures the annuloplasty ring and adjustment suture during shipment. The end user may later remove the annuloplasty ring and its adjustment suture from the support. Although some existing annuloplasty ring supports have been adequate thus far, improvements to these supports are desirable.

BRIEF SUMMARY OF THE INVENTION

The present disclosure relates to a support for an adjustable annuloplasty ring. An embodiment of the support generally includes a body and a groove. The body of the support has a first end, a second end, an outer surface and an inner surface. The inner surface defines a longitudinal bore. The outer surface is configured to receive an annuloplasty ring. The groove is formed along at least a portion of the outer surface of the body and is dimensioned to receive at least a portion of a suture.

The present disclosure also relates to an annuloplasty system including a support, an adjustable annuloplasty ring, and a suture. The support includes a body and a groove. The body of the support has a first end, a second end, an outer surface and an inner surface. The inner surface defines a longitudinal bore. The groove is formed along at least a portion of the outer surface of the body. The adjustable annuloplasty ring is positioned around the outer surface of the body of the support. The suture is at least partially wound around the outer surface of the body. The suture has first and second ends adapted to be received within the groove of the support.

The present disclosure further relates to a method for handling an annuloplasty ring. An exemplary embodiment of this method includes providing a support including a body having an outer surface and an inner surface defining a longitudinal bore, and a groove formed along at least a portion of the outer surface of the body; positioning an annuloplasty ring around the outer surface of the body of the support; winding a suture around the outer surface of the body of the support; and securing ends of the suture inside the groove of the support.

Moreover, the present disclosure relates to a method for manufacturing an annuloplasty ring system. An embodiment of this method includes providing a support including a body having an outer surface and an inner surface defining a longitudinal bore, and a groove formed along at least a portion of the outer surface of the body; positioning an annuloplasty ring around the body of the support; winding a suture around the body of the support in a coiled configuration; and heat setting the annuloplasty ring after positioning the annuloplasty ring around the support.

BRIEF DESCRIPTION OF THE DRAWINGS

Various embodiments of the present invention will now be discussed with reference to the appended drawings. It is appreciated that these drawings depict only some embodiments of the invention and are therefore not to be considered limiting of its scope.

DETAILED DESCRIPTION

Figure 1:
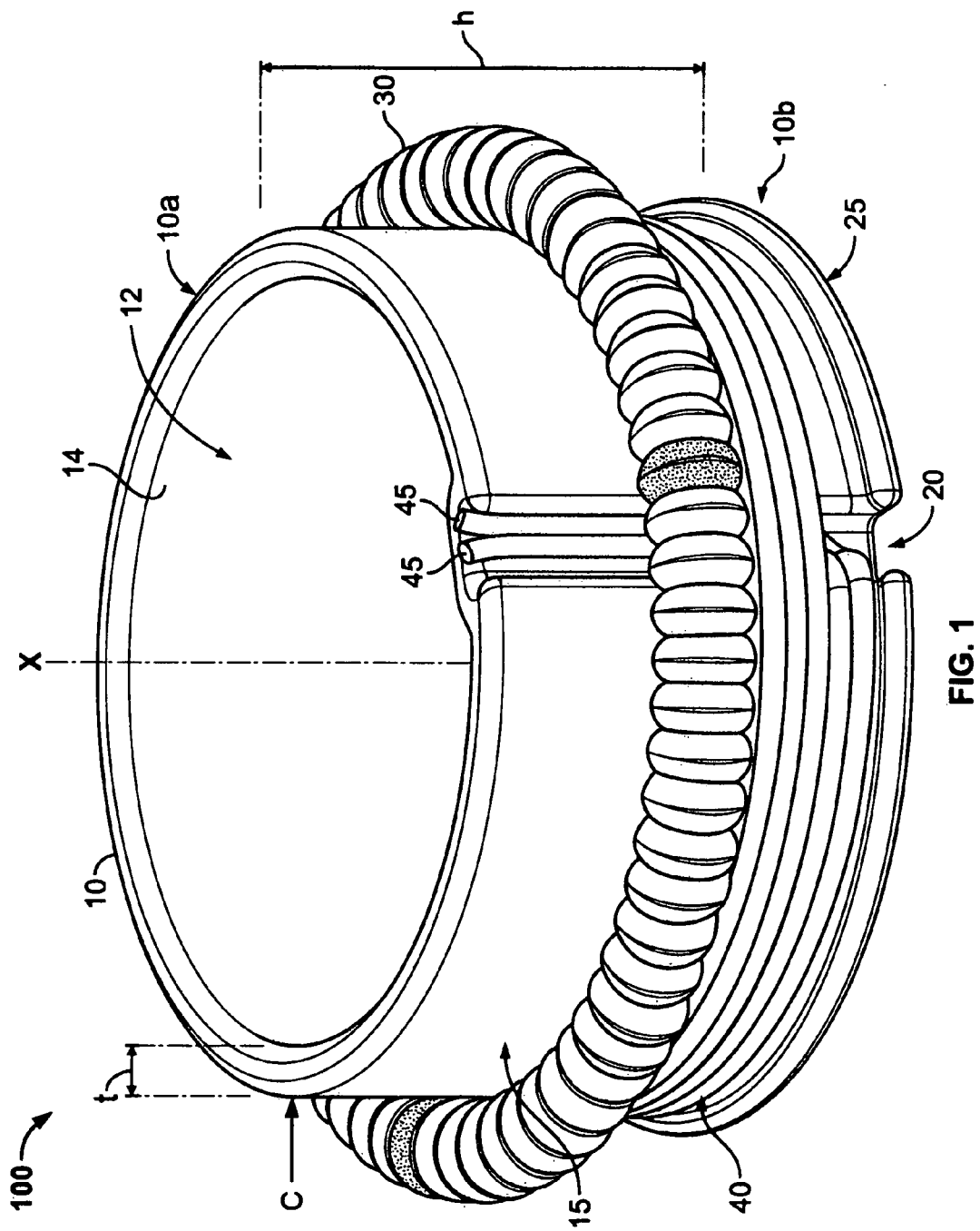
FIG. 1 is a perspective view of a support for an adjustable annuloplasty ring with an adjustable annuloplasty ring positioned around the support in accordance with an embodiment of the present disclosure.
Figure 2:
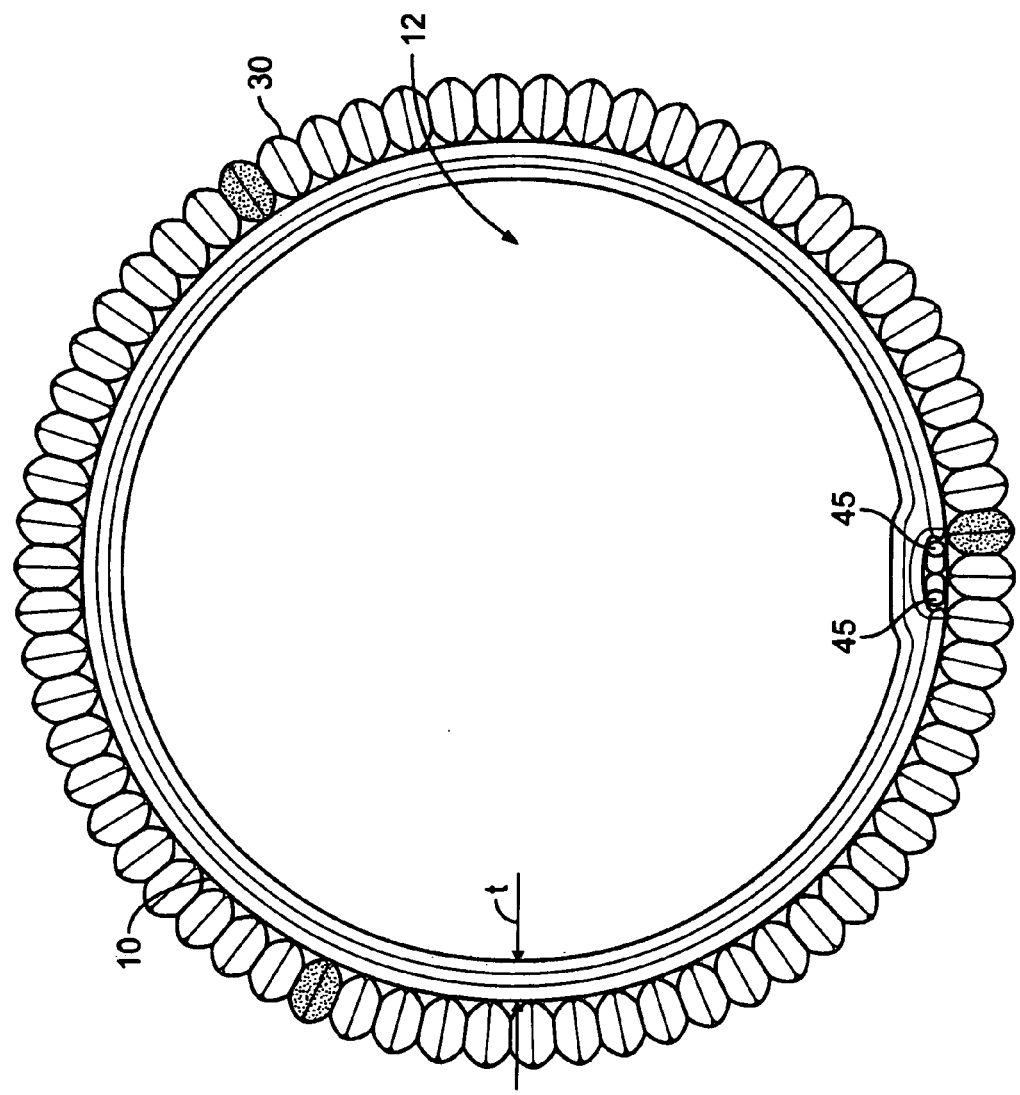
FIG. 2 is a top view of the support of FIG. 1 with an adjustable annuloplasty ring positioned around the support.

FIGS. 1 and 2 illustrate a support 100 for supporting an adjustable annuloplasty ring 30. Support 100 generally includes a body 10, a longitudinal bore 12 extending through body 10, and a groove 20 formed along at least a portion of body 10. In some embodiments, support 100 may be wholly or partly made of a substantially rigid material, but support 100 alternatively may be formed from any material suitable for maintaining the geometry of adjustable annuloplasty ring 30.

Body 10 has a first end 10a and a second end 10b and includes an inner surface 14 and an outer surface 15 configured to slidably receive adjustable annuloplasty ring 30. Outer surface 15 surrounds inner surface 14 and may have a substantially smooth surface structure. Inner surface 14 defines longitudinal bore 12. Longitudinal bore 12 may extend from the first end 10a to the second end 10b of body 10 along a longitudinal axis X and may have a substantially cylindrical shape or round cross-section, as shown in FIG. 2.

In certain embodiments, body 10 further includes a lip 25 located at its second end 10b and protruding away from longitudinal bore 12. Lip 25 may extend along the entire or substantially the entire perimeter of second end 10b of body 10 and is adapted to prevent adjustable annuloplasty ring 30 from sliding off body 10 during manufacture, shipping, or use. Alternatively, lip 25 may extend along only a part of the perimeter of body 10. In the embodiment depicted in FIG. 1, lip 25 surrounds the entire perimeter of second end 10b except for the portion of body 10 containing groove 20.

Groove 20 extends along at least part of outer surface 15 of body 10 and is dimensioned and configured for securely receiving at least portions of a suture 40. In certain embodiments, groove 20 extends from first end 10a to second end 10b of body 10 along its outer surface 15. Groove 20 may be oriented substantially parallel to the longitudinal axis X defined by longitudinal bore 12. Alternatively, the orientation of groove 20 may define an oblique angle relative to longitudinal axis X. In either event, groove 40 can secure at least the ends 45 of suture 40, as shown in FIG. 1. Although two suture ends 45 are illustrated in FIG. 1, an alternate adjustable annuloplasty ring may contain greater or fewer than two suture ends, and therefore greater or fewer than two suture ends 45 may be secured in groove 40.

Although FIG. 1 shows a support 100 with a substantially round or cylindrical body 10, body 10 may have other suitable shapes. The shape of body 10 may depend on the desired final shape of adjustable annuloplasty ring 30. For instance, body 10 may have a non-round shape.

Irrespective of its shape, body 10 features a thickness t suitable for maintaining the geometry of adjustable annuloplasty ring 30 during the manufacturing process, which may include sterilization and/or heat setting. Thickness t constitutes the distance between outer surface 15 and inner surface 14. In addition, body 10 has a height h sufficient to (1) retain adjustable annuloplasty ring 30 and suture 40 during manufacture and shipping, and (2) make the presence of support 100 obvious to an end user, thereby reminding the end user to remove support 100 before implanting ring 30 in a patient. Height h constitutes the distance between first end 10a and second end 10b of body 10.

In alternate configurations of support 100, longitudinal bore 12 does not extend fully from first end 10a to second end 10b. For instance, some portion of height h may have a solid cross section. This solid cross section could be positioned adjacent to first end 10a, adjacent to second end 10b, or at any location between first end 10a and second end 10b. This solid cross section may further remind the user that the support is to be removed before implanting annuloplasty ring 30 in a patient. Alternatively, longitudinal bore 12 may extend fully from first end 10a to second end 10b in some portion of the center of support 100. For instance, a cross or "x" geometry may exist in the center of support 100. This geometry may either extend fully from first end 10a to second end 10b or may extend along some portion of height h.

Alternatively, support 100 may not include an inner surface 14 and longitudinal bore 12, in which case support 100 would take the form of a solid cylinder.

Body 10 also has a perimeter or circumference C (where body 10 is circular) sufficient to contact or engage an inner perimeter or circumference of adjustable annuloplasty ring 30 and maintain the geometry of ring 30. Perimeter or circumference C may vary according to the perimeter or circumference of adjustable annuloplasty ring 30. Perimeter C may be round or may have any other suitable non-round shape, depending on the desired final shape for adjustable annuloplasty ring 30.

Aside from supporting adjustable annuloplasty ring 30, body 10 of support 100 is adapted to manage adjustment suture 40. Adjustment suture 40 may be attached to adjustable annuloplasty ring 30 and may extend from adjustable annuloplasty ring 30 any suitable distance. For example, adjustment suture 40 may extend from adjustable annuloplasty ring 30 about twelve to eighteen inches or more. Body 10 may have any shape suitable to arrange adjustment suture 40 in a smooth configuration, for instance a coil, around support 100. To achieve this configuration, adjustment suture 40 may be wound around outer surface 15 of body 10 during the manufacturing process. Due to its compact and consistent configuration, adjustment suture 40 does not interfere with the eventual use of adjustable annuloplasty ring 30 and permits support 100 and adjustable annuloplasty ring 30 to be contained in a relatively small sterile package, such as a sterilization tray or a pouch. In certain embodiments, outer surface 15 is substantially smooth to prevent, or at least inhibit, the formation of sharp bends or kinks in adjustment suture 40. Sharp bends and kinks in adjustment suture 40 may interfere with the end user's ability to use adjustable annuloplasty ring 30 properly. The substantially smooth surface also allows the adjustable annuloplasty ring 30 and adjustment suture 40 to be easily slid off body 10 by the end user. Alternatively, outer surface 15 may be roughened to prevent, or at least hinder, slippage of adjustment suture 40 or adjustable annuloplasty ring 30 from body 10. For instance, a surface roughness of Ra 63 to 500 may hinder movement of the adjustable annuloplasty ring 30 and adjustment suture 40 during shipment, but not significantly inhibit ease of sliding off body 10 by the end user.

As discussed above, groove 20 is configured to secure the ends 45 of adjustment suture 40 and, consequently, prevents, or at least hinders, suture 40 from slipping off of body 10. Securing ends 45 in groove 20 may allow adjustment suture 40 to maintain its compact configuration when, for example, the user opens a sterile package containing support 100 and adjustable annuloplasty ring 30. Maintaining adjustment suture 40 in a compact configuration also prevents, or at least minimizes, the premature unwinding or expansion of suture 40 into an undesired location, such as outside the sterile field.

Support 100 can physically hold adjustable annuloplasty ring 30 even before the manufacturing process is completed and until the end user is ready to deploy adjustable annuloplasty ring 30. A manufacturer may employ any suitable process to fabricate adjustable annuloplasty ring 30. Adjustable annuloplasty ring 30 may be placed around the outer surface 15 of body 10 during the assembly of adjustable annuloplasty ring 30 or after adjustable annuloplasty ring 30 has been fully assembled. Adjustment suture 40 may also be positioned around the outer surface 15 of body 10 during assembly of the adjustable annuloplasty ring 30 or after the adjustable annuloplasty ring 30 has been fully assembled. For instance, adjustment suture 40 may be wound around body 10 in a coiled configuration after adjustable annuloplasty ring 30 has been fully assembled. Adjustable annuloplasty ring 30 and/or adjustment suture 40 may reside on body 10 of support 100 throughout the entire manufacturing and shipping processes until adjustable annuloplasty ring 30 is removed from support 100 by the end user.

As discussed above, the process of manufacturing adjustable annuloplasty ring 30 and adjustment suture 40 may include sterilization and heat setting. Adjustable annuloplasty ring 30 and/or adjustment suture 40 may be positioned around body 10 of support 100 before commencing the sterilization and/or heat setting steps. Support 100 may therefore serve to set a limit on the dimension to which annuloplasty ring 30 and adjustment suture 40 may shrink during manufacture. The ends 45 of suture 40 may be secured within groove 20 of support 100 before, during or after sterilizing and/or heat setting.

Support 100 may also prevent, or at least minimize, the occurrence of sharp bends or kinks in adjustment suture 40 during the manufacturing process. Adjustment suture 40 may permanently set during either sterilization or heat setting. As a consequence, the formation of sharp bends or kinks in adjustment suture 40 should be avoided at this stage. In some embodiments, the outer surface 15 of body 10 has a round, smooth configuration for facilitating winding of suture 40 around body 10 in a coiled configuration. The coiled configuration of adjustment suture 40 minimizes the risk of forming sharp bends or kinks.

Support 100 may be utilized in lieu of a heat set mandrel during sterilization and heat setting. By eliminating the use of a heat set mandrel, adjustment suture 40 and/or adjustable annuloplasty ring 30 do not have to be transferred from a mandrel to support 100, thereby streamlining the manufacturing process. In addition, the use of support 100 lessens the amount of manipulation of adjustable annuloplasty ring 30 and adjustment suture 40 during the manufacturing process. Moreover, using support 100 ensures a more consistent and properly configured final product, as removing adjustable annuloplasty ring 30 and adjustment suture 40 from the mandrel during the manufacture of the apparatus increases the likelihood that adjustment suture 40 will lose its desired configuration.

Once the manufacturing process has been completed, an annuloplasty ring system including adjustable ring 30, support 100, and suture 40 may be assembled in any suitable container, such as a sterile package, and then shipped to the distributor or end user. The end user can employ this annuloplasty ring system to repair a mitral or tricuspid valve. In doing so, the end user slides adjustable annuloplasty ring 30 and suture 40 along the outer surface 15 of body 10 to separate adjustable annuloplasty ring 30 from support 100. In the process of sliding the ring 30 and suture 40 off the support 100, the end user removes the ends of suture 40 from groove 20. Thereafter, the end user places and adjusts annuloplasty ring 30 in a patient to repair her mitral or tricuspid valve.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, persons skilled in the art will envision other positions for groove 20, other shapes for support 100, or other configurations for adjustment suture 40.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A support for an adjustable annuloplasty ring, comprising:
a body having a first end, a second end, a length between the first end and the second end, an outer surface, and an inner surface defining a longitudinal bore extending at least partially between the first end and the second end, the outer surface and the inner surface collectively defining a wall thickness of the body, the outer surface being configured to receive an annuloplasty ring; and
a groove formed along at least a portion of the outer surface of the body and dimensioned to receive at least a portion of a suture, the groove having a depth from the outer surface that is less than the wall thickness of the body and less than the length of the body.

2. The support according to claim 1, wherein the groove extends from the first end of the body to the second end of the body.

3. The support according to claim 1, further comprising a lip at the second end of the body.

4. The support according to claim 3, wherein the lip surrounds a majority of a perimeter of the second end of the body.

5. The support according to claim 1, wherein the outer surface of the body is smooth.

6. The support according to claim 1, wherein the outer surface of the body is roughened.

7. The support according to claim 1, wherein the body has a substantially cylindrical shape.

8. The support according to claim 1, wherein the longitudinal bore has a longitudinal axis and the groove is oriented parallel to the longitudinal axis.

9. An annuloplasty system, comprising:
a support including:
a body having a first end, a second end and an outer surface;
a groove formed along at least a portion of the outer surface of the body;
an adjustable annuloplasty ring positioned around the outer surface of the body; and
a suture at least partially wound around the outer surface of the body in contact with the outer surface of the body, the suture having first and second ends adapted to be received within the groove.

10. The system according to claim 9, wherein the groove extends from the first end of the body to the second end of the body.

11. The system according to claim 9, further including a lip at the second end of the body.

12. The system according to claim 11, wherein the lip surrounds a majority of a perimeter of the second end of the body.

13. The system according to claim 9, wherein the outer surface of the body is smooth.

14. The system according to claim 9, wherein the body has a substantially cylindrical shape.

15. The system according to claim 9, wherein the body further includes an inner surface defining a longitudinal bore extending at least partially between the first end and the second end.

16. The system according to claim 15, wherein the longitudinal bore has a longitudinal axis and the groove is oriented parallel to the longitudinal axis.

* * * * *